United States Patent [19]

Meyer

[11] 3,993,659

[45] Nov. 23, 1976

[54] BIS-BENZOXAZOLYL-NAPHTHALENES AS OPTICAL BRIGHTENERS

[75] Inventor: Hans-Rudolf Meyer, Binningen, Switzerland

[73] Assignee: Ciba-Geigy Corporation, Ardsley, N.Y.

[22] Filed: Feb. 7, 1975

[21] Appl. No.: 548,043

Related U.S. Application Data

[63] Continuation-in-part of Ser. No. 502,681, Sept. 3, 1974, abandoned, which is a continuation of Ser. No. 276,992, Aug. 1, 1972, abandoned.

[30] Foreign Application Priority Data

Aug. 10, 1971 Switzerland ........................ 11709/71

[52] U.S. Cl. ............................ 260/307 D; 106/176; 260/45.8 NZ; 260/307 C; 260/456 R; 260/456 A; 260/456 P

[51] Int. Cl.$^2$ ........................................ C07D 263/56

[58] Field of Search ................................ 260/307 D

[56] References Cited

UNITED STATES PATENTS

| | | | |
|---|---|---|---|
| 3,644,345 | 2/1972 | Siegrist et al. | 260/240 CA |
| 3,682,946 | 8/1972 | Liechti | 260/307 D |
| 3,767,664 | 10/1973 | Weber | 260/307 D |

FOREIGN PATENTS OR APPLICATIONS

| | | |
|---|---|---|
| 1,163,851 | 9/1969 | United Kingdom |

*Primary Examiner*—Raymond V. Rush
*Attorney, Agent, or Firm*—Joseph G. Kolodny; Edward McC. Roberts; Prabodh I. Almaula

[57] ABSTRACT

1,4-Bis-benzoxazolyl-(2)′-naphthalenes of the formula

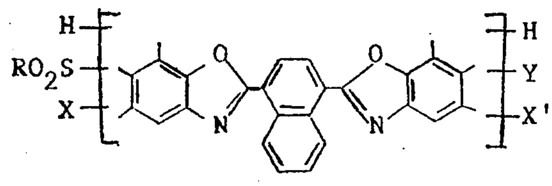

wherein R denotes optionally non-chromophorically substituted alkyl with 1 to 18 carbon atoms, alkenyl with 2 to 4 carbon atoms, cycloalkyl, aryl or aralkyl, Y denotes hydrogen, alkyl with 1 to 4 carbon atoms, halogen, carboxyl, carbalkoxy with 2 to 5 carbon atoms or the radical —$SO_2R'$, wherein R′ represents optionally non-chromophorically substituted alkyl with 1 to 18 carbon atoms, cycloalkyl, alkenyl with 2 to 4 carbon atoms, aryl or aralkyl, and X and X′ independently of one another denote hydrogen, chlorine or alkyl with 1 to 4 carbon atoms. These new compounds are useful as optical brighteners for organic materials, especially for polyesters, polyvinyl chloride, polystyrene, polyacrylonitrile and cellulose acetates.

5 Claims, No Drawings

BIS-BENZOXAZOLYL-NAPHTHALENES AS OPTICAL BRIGHTENERS

This application is a continuation-in-part of copending application Ser. No. 502,681, filed Sept. 3, 1974, now abandoned which application is a continuation of Ser. No. 276,992, filed Aug. 1, 1972, now abandoned.

The present invention relates to new 1,4-bis-benzoxazoly-(2')-naphthalenes, their use for the optical brightening of organic materials, and processes for their manufacture.

These new 1,4-bis-benzoxazolyl-(2')-naphthalenes correspond to the formula (1)

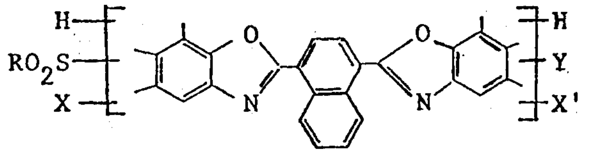

wherein R denotes optionally non-chromophorically substituted alkyl with 1 to 18, preferably 1 to 6, especially 1 to 4, carbon atoms, alkenyl with 2 to 4 carbon atoms, cycloalkyl, preferably cyclohexyl, aryl or aralkyl, Y denotes hydrogen, alkyl with 1 to 4 carbon atoms, halogen, preferably chlorine, carboxyl, carbalkoxy with 2 to 5 carbon atoms or the radical $-SO_2R'$, wherein R' is identical to R or different from R and represents optionally non-chromophorically substituted alkyl with 1 to 18, preferably 1 to 6, especially 1 to 4, carbon atoms, cycloalkyl, preferably cyclohexyl, alkenyl with 2 to 4 carbon atoms, aryl or aralkyl, and X and X' independently of one another denote hydrogen, halogen, preferably chlorine, or alkyl with 1 to 4 carbon atoms.

As non-chromophoric radicals which may be present as substituents of the alkyl radical R, there should above all be mentioned hydroxyl, nitrile, chlorine, sulpho, carboxyl, alkoxy with 1 to 18, preferably 1 to 4, carbon atoms, aryloxy, aralkyloxy, alkenyloxy, carbalkoxy with 2 to 19, preferably 2 to 5, carbon atoms, carbaryloxy and carbaralkyloxy. Examples of such substituted alkyl radicals are 2-hydroxyethyl, 2,3-dihydroxypropyl, $-CH_2COOCH_2C_6H_5$, $-CH_2COOC_6H_5$, $-CH_2CH_2COOCH_2C_6H_5$, $-CH_2CH_2COOC_6H_5$, carbalkoxy(1-4C)methyl, carbalkoxy(1-4C)ethyl, cyanomethyl, cyanoethyl, alkoxy(1-4C)ethyl, phenoxyethyl, benzyloxy-ethyl, vinyloxyethyl, dichloromethyl, 2-sulphoethyl, 3-sulpho-propyl and 4-sulphobutyl (or their salts, such as sodium, potassium and ammonium salts).

The preferred aryl radical (in the definition of R and R') is phenyl or diphenyl optionally substituted by non-chromophoric groups. Possible non-chromophoric substituents are above all alkyl or alkoxy with 1 to 4 carbon atoms and also halogen, preferably chlorine. The number of these non-chromophoric substituents per phenyl radical in general does not exceed the number 2.

Aralkyl radicals are in general phenylalkyl with 1 to 4 C atoms in the alkyl part, optionally substituted in the phenyl ring by halogen, preferably chlorine, alkyl or alkoxy with 1 to 4 C atoms, such as benzyl, chlorobenzyl and dichlorobenzyl, and also diphenylmethyl and triphenylmethyl.

Vinyl, allyl, methallyl and crotyl may be mentioned as examples of alkenyl radicals.

The symbols Y preferably represents the sulphone radical $-SO_2R'$.

Within the framework of the formula (1), the compounds which are symmetrical relative to the naphthyl radical, that is to say those in which $X = X'$ and $-SO_2R = Y = SO_2R'$, and in which these substituents are in the appropriate positions, should be particularly singled out.

The compounds of the formula (2)

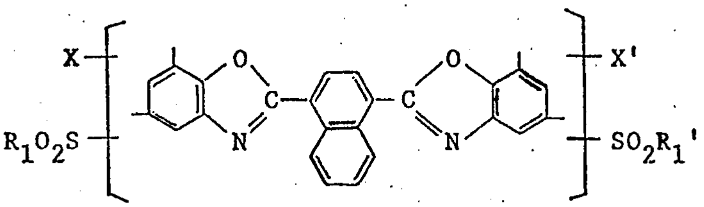

wherein $R_1$ and $R_1'$ independently of one another denote alkyl with 1 to 6, preferably 1 to 4, carbon atoms which is optionally substituted by chlorine, phenyl which is optionally substituted by chlorine or alkyl with 1 to 4 carbon atoms or phenylalkyl with 1 to 3 carbon atoms in the alkyl part which is optionally substituted by chlorine or methyl at the phenyl, and X and X' independently of one another denote hydrogen, chlorine or alkyl with 1 to 4 carbon atoms, should be singled out.

Preferred symmetrical compounds within the framework of the formula (2) correspond to the formula (3)

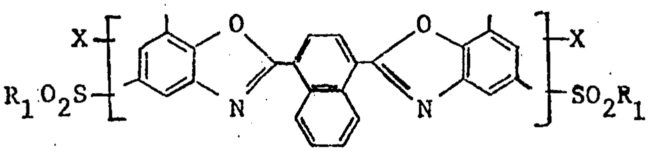

wherein $R_1$ and X have the above mentioned meaning.

Particularly interesting compounds of symmetrical and asymmetrical nature fall under the formula (4) 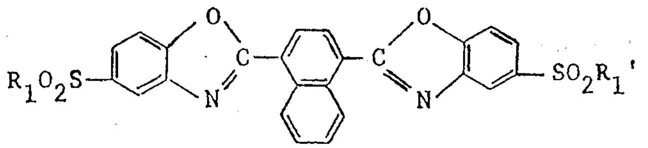

wherein $R_1$ and $R_1'$ have the indicated meaning.

Compounds of industrial interest are above all the symmetrical compounds of the formula (5) 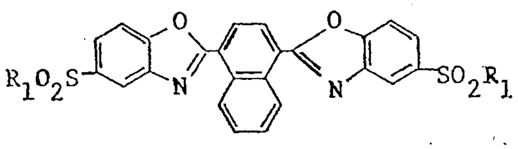

wherein $R_1$ has the indicated meaning.

Compounds of particular practical interest are those of the formula (6) 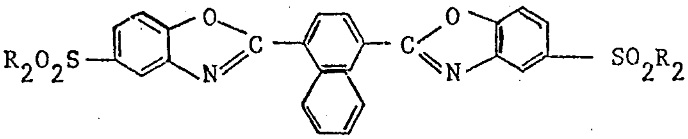

wherein $R_2$ denotes methyl, ethyl, phenyl or benzyl.

The 1,4-bis-benzoxazolyl-(2')-naphthalenes characterised above can be manufactured according to various processes which are in themselves known. For example, the process of oxazole ring closure is employed, starting from the appropriate acylamides. In its most general form, this procedure can be defined as subjecting compounds of the formula (7) 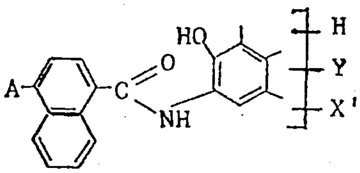

wherein A represents a radical having the meaning (8) 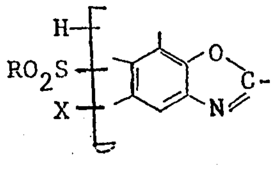

or (9) 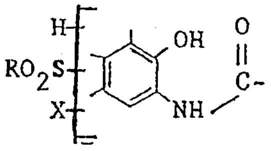

or a compound of the formula

(10) 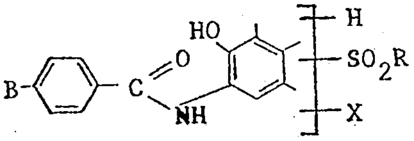

wherein B represents a radical having the meaning

(11) 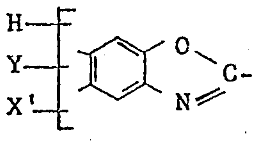 or (12) 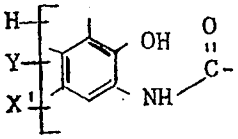

and R, Y, X and X' have the indicated meaning, to the ring closure reaction by heating to temperatures above 100° C, optionally in the presence of a catalyst.

As can be seen, the variant first mentioned for A and for B is in particular relevant to the synthesis of compounds of the formula (1) which are asymmetrically substituted relative to the naphthalene ring system.

On the other hand, for the synthesis of symmetrical compounds, the second variant is above all used in practice, that is to say acyl compounds of the formula

(13) 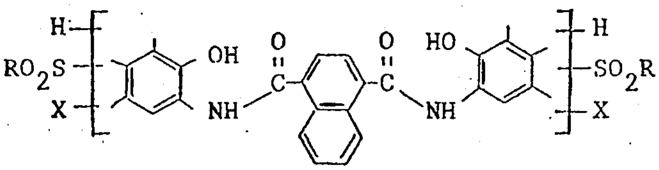

are subjected to the ring closure reaction by heating to temperatures above 100° C, in the presence of catalysts if appropriate.

To manufacture the acyl compounds of the formula (7), (10) and (13) required for the process described above, a compound of the formula

(14) 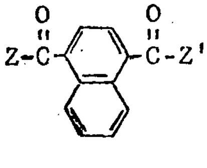

wherein Z and Z' independently of one another represent hydroxyl, halogen (preferably chlorine) or an alkoxy group with 1 to 4 carbon atoms, is reacted with aminophenols of the formulae

(15) 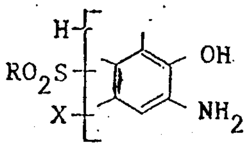

and

(16) 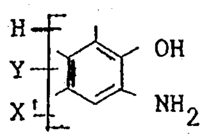

wherein R, Y, X and X' have the indicated meaning.

Instead of the aminophenols of the formulae (9) and (10), their oxazolones, of the formulae

(17) 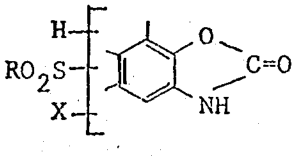

or (18) 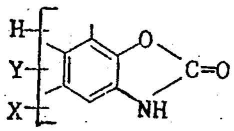

can also be employed.

Depending on whether the manufacture of asymmetrical or symmetrical types is intended, Z≠Z' or Z=Z' will be chosen, and it is appropriate to prefer functions of distinctly differing reactivity, for example the acid ester chloride, for the case of Z ≠ Z', and compounds which are as reactive in nature as possible, that is to say, for example, the dicarboxylic acid chloride, for the case of Z=Z'.

If it is desired to manufacture asymmetrical types, an appropriate procedure is first to carry out a one-sided ring closure on the primary condensation product of the formula

(19) 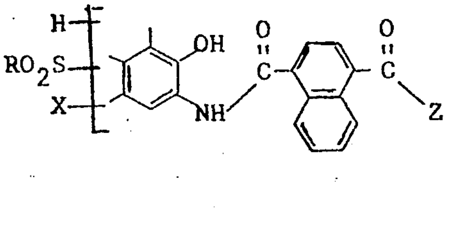

or

(20) 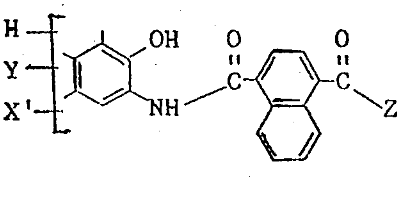

wherein R, Y, X, X' and Z have the indicated meaning, analogously to the manner indicated above, to give compounds of the formula

(21) 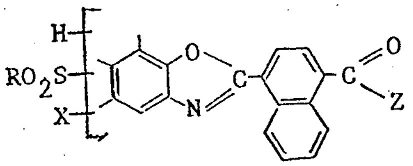

or

(22) 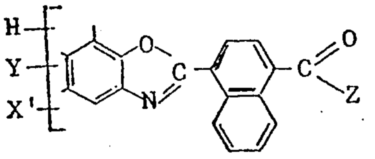

and then to repeat the analogous reaction sequence with an aminophenol of the formula (16) or (15 ) on the remaining carboxyl function

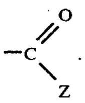

The synthesis of compounds according to the general formula (1) and to the formula of sub-categories of compounds can in principle also be carried out in a one-step process, starting from o-aminophenols of the formula (16) or (15) and naphthalene-1,4-dicarboxylic acid derivatives of the formula (14), by heating these components together to higher temperatures, appropriately between 120° and 350° C, in an inert gas (for example a stream of nitrogen). This reaction is preferably carried out in the presence of agents which split off water, in the same way as described above for the final stage.

To manufacture symmetrical types, a two-stage process is preferably used, in which firstly o-aminophenols of the formula (15) and naphthalenedicarboxylic acid compounds of the formula (14) (wherein Z=Z') are condensed to give acyl compounds of the formula (13). For this, the naphthalenedicarboxylic acid chlorides are appropriately used, which are condensed with the aminophenols at temperatures of between 100° and 220° C in the presence of an organic solvent such as toluene, xylene, chlorobenzene, dichlorobenzene, trichlorobenzene or nitrobenzene or in an inert amine such as pyridine, picolines, triethylamine, quinoline, N,N-dimethylaniline and the like, which bind the hydrogen halide liberated, the resulting acyl compounds of the formula (13) then being converted into the azole derivatives at temperatures of between 120° and 350° C, if necessary in the presence of a catalyst. If carboxylic acid chlorides are used as starting substances, these can be manufactured immediately prior to the condensation with the 0-amino compound, and without isolation, from the free carboxylic acid and thionyl chloride, optionally with addition of a catalyst, such as pyridine, in the solvent wherein the condensation subsequently takes place.

Suitable agents for splitting off water, including catalysts having the effect of splitting off water, are, for example, boric acid, boric anhydride, zinc chloride, p-toluenesulphonic acid, phosphorus oxychloride, phosphorus trichloride, thionyl chloride and polyphosphoric acids, including pyrophosphoric acid. It is also possible conjointly to employ high-boiling polar organic solvents such as, for example, dimethylformamide, dichlorobenzene, trichlorobenzene, chlorinated biphenyl and aliphatic optionally etherified hydroxy compounds, for example propylene glycol, ethylene glycol monoethyl ether and high-boiling esters of phthalic acid, such as, for example, phthalic acid dibutyl ester.

A particularly advantageous process for the manufacture of compounds of the formula (3) is, for example, to subject the acyl compounds obtained by condensation of 2 mols of o-aminophenols of the formula

(23) 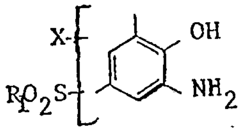

wherein $R_1$ and X have the indicated meaning, with naphthalene-1,4-dicarboxylic acid dichloride, in the presence of agents which split off water, without isolation, to an azole ring closure reaction by treatment with the same agent for splitting off water as is used in the preliminary stage, at temperatures of between 120° and 350° C.

Amongst further possible manufacturing processes, the reaction of 1,4-dicyanonaphthalene with o-aminophenols of the formula (15) or (16) at elevated temperatures, preferably 160° to 260° C, may be mentioned. This reaction is appropriately carried out in the presence of agents which bind ammonia such as, for example, phosphoric acid, polyphosphoric acid or phosphorus pentoxide, under an inert gas.

Another manufacturing process for compounds of the formula (1) which is advantageous in many cases consists of the condensation of o-halogenoanilines with a compound of the formula (14) according to the equation

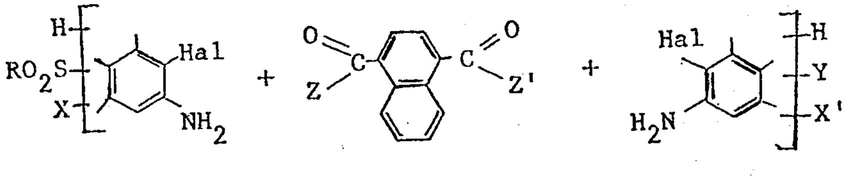

(24) (14) (25)

in accordance with methods which are in themselves known, to give the corresponding acid amide of the formula

(26) 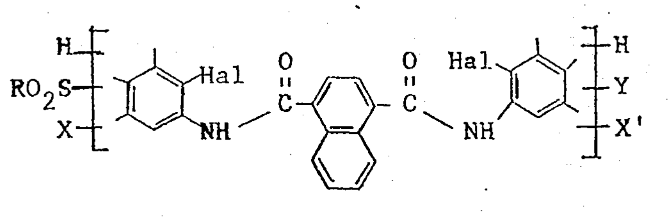

and subsequent ring closure to give the corresponding bisbenzoxazolyl derivative. The ring closure reaction is here carried out in the presence of polar solvents which are chemically inert towards the reactants, and also in the presence of agents which bind hydrogen halide, and of copper catalysts. In the above formulae, Hal here denotes chlorine or bromine, whilst all the remaining symbols have the meaning indicated above.

This manufacturing process proves particularly appropriate for the preparation of symmetrical compounds of the formulae (3), (5) and (6).

As examples of polar solvents which are chemically inert towards the reactants there may be mentioned dimethylformamide, dimethylsulphoxide, N-methylpyrrolidone or nitrobenzene. As agents which bind hydrogen halide there may be mentioned: alkali acetate, magnesium oxide, organic bases such as pyridine and the like. As examples, copper-I chloride, copper-II chloride, copper acetate, copper oxides, elementary finely divided copper and the like may be mentioned as copper catalysts.

The starting products of the formulae (14) to (16) are known or are manufactured analogously to processes which are in themselves known.

The 2-amino-alkylsulphonyl-phenols used as starting products can be manufactured, for example, as follows: 4-chloro-alkylsulphones are nitrated in the 3-position (U.S. Pat. No. 2,938,042; British Pat. No. 467,549), the chlorine is saponified with sodium hydroxide solution and the nitro group is reduced (British Patent No. 647,168). It is also possible to reduce benzoxazolone-sulphonyl chloride with sodium sulphite to the sulphinic acid, alkylate the latter with lower dialkyl sulphates or alkyl halides and saponify the resulting alkylsulphonylbenzoxazolones with sodium hydroxide solution (D. Simov et. al. C.A. 66 (1967) 115,401 m). This process is also particularly suitable for the manufacture of 5- or 6-alkylsulphonyl-2-amino-phenols. The synthesis of 2-amino-4-chloromethylsulphonyl-phenol is carried out similarly to the methods first described (British Patent No. 720,251).

The arylsulphonyl-aminophenols are obtained, for example, according to examples in British Patent No. 743,907 by Friedel-Crafts reaction of 4-chloro-3-nitrobenzenesulphonyl chloride with the corresponding aromatic compounds (benzene, toluene, xylene, mesitylene and the like), in which, for example, the condensation predominantly takes place in the 4-position in the case of toluene or m-xylene but can in addition also take place in the 2-position. In the case of chlorobenzene (J. D. Loudon, T. D. Robson, J. Chem. Soc. 1937 242–246) or toluene (J. D. Loudon, J. Chem. Soc. 1936 218–222), anhydrous iron chloride is advantageously used as the catalyst instead of aluminium chloride, in which case less than molar amounts of sulphonyl chloride also suffice. The resulting chloro-3-nitrophenylarylsulphones are then converted, analogously to the 4-chloro-3-nitrophenylalkylsulphones, into the corresponding aminophenols.

2-Amino-aralkylsulphonyl-phenols are obtained in a similar manner to the 2-amino-alkylsulphonylphenols (British Patent No. 743,907). For example, 4-chloro-3-nitrobenzenesulphinic acid is heated with benzyl chloride (slight excess) to 80° –85° C whilst constantly neutralising, with sodium hydroxide solution, the hydrochloric acid formed, and the resulting 4-chloro-3-nitrophenyl-benzylsulphone is converted into the corresponding aminophenol as previously described.

The new compounds defined above show a more or less pronounced fluorescence in the dissolved or finely divided state. They can be used for the optical brightening of the most diverse synthetic, semi-synthetic or natural organic materials, or substances which contain such organic materials.

The following groups of organic materials, where optical brightening thereof is relevant, may be mentioned as examples of the above, without the survey given below being intended to express any restriction thereto:

I. Synthetic organic high molecular materials:

a. Polymerisation products based on organic compounds containing at least one polymerisable carbon-carbon double bond, that is to say their homopolymers or copolymers as well as their after-treatment products such as, for example, crosslinking. grafting or degradation products, polymer blends or products obtained by modification of reactive groups, for example polymers based on $\alpha,\beta$-unsaturated carboxylic acids or derivatives of such carboxylic acids, especially on acrylic compounds (such as, for example, acrylic esters, acrylic acid, acrylonitrile, acrylamides and their derivatives or their methacryl analogues), on olefine hydrocarbons (such as, for example, ethylene, propylene, styrenes or dienes and also so-called ABS polymers), and polymers based on vinyl and vinylidene compounds (such as, for example, vinyl chloride, vinyl alcohol or vinylidene chloride), b. Polymerisation products which are obtainable by ring opening, for example, polyamides of the polycaprolactam type, and also polymers which are obtainable both via polyaddition and via polycondensation, such as polyethers or polyacetals, c. Polycondensation products or precondensates based on bifunctional or polyfunctional compounds possessing condensable groups, their homocondensation and co-condensation products, and after-treatment products, such as, for example, polyesters, especially saturated (for example ethylene glycol terephthalic acid polyesters) or unsaturated (for example maleic acid dialcohol polycondensates as well as their crosslinking products with copolymerisable vinyl monomers), unbranched or branched (also based on high-functional alcohols, such as, for example, alkyd resins) polyesters, polyamides (for example hexamethylenediamine adipate), maleate resins, melamine resins, their precondensates and analogues, polycarbonates and silicones d. Polyaddition products such as polyurethanes (crosslinked and non-crosslinked) and epoxide resins.

II. Semi-synthetic organic materials, for example, cellulose esters of varying degrees of esterification (so-called 2½-acetate or triacetate) or cellulose ethers, regenerated cellulose (viscose or cuprammonium cellulose), or their after-treatment products, and cascin plastics.

III. Natural organic materials of animal or vegetable origin, for example based on cellulose or proteins such as cotton, wool, linen, silk, natural lacquer resins, starch and casein.

The organic materials to be optically brightened can be in the most diverse states of processing (raw materials, semi-finished goods or finished goods). On the other hand, they can be in the form of structures of the most diverse shapes that is to say, for example, as predominantly three-dimensional bodies such as sheets, profiles, injection mouldings, various machined articles, chips, granules or foams, and also as predominantly two-dimensional bodies such as films, foils, lacquers, coatings, impregnations and coatings, or as predominantly one-dimensional bodies such as filaments, fibres, flocks and wires. The said materials can, on the other hand, also be in an unshaped state, in the most diverse homogeneous or inhomogeneous forms of division, such as, for example, in the form of powders, solutions, emulsions, dispersions, latices, pastes or waxes.

Fibre materials can, for example, be in the form of endless filaments (stretched or unstretched), staple fibres, flocks, hanks, textile filaments, yarns, threads, fibre fleeces, felts, waddings, flock structures or woven textile fabrics, textile laminates, knitted fabrics and papers, cardboards or paper compositions.

The compounds to be used according to the invention are of importance, inter alia, for the treatment of organic textile materials, especially woven textile fabrics. Where fibres, which can be in the form of staple fibres or endless filaments or in the form of hanks, woven fabrics, knitted fabrics, fleeces, flock substrates or laminates, are to be optically brightened according to the invention, this is advantageously effected in an aqueous medium, wherein the compounds in question are present in a finely divided form, (suspensions, so-called micro-dispersions or possibly solutions) If desired, dispersing agents, stabilisers, wetting agents and further auxiliaries can be added during the treatment.

Depending on the type of brightener compound used, it may prove advantageous to carry out the treatment in a neutral or alkaline or acid bath. The treatment is usually carried out at temperatures of about 20° to 140° C, for example at the boiling point of the bath or near it (about 90° C). Solutions or emulsions in organic solvents can also be used for the finishing, according to the invention, of textile substrates as is practised in the dyeing trade in so-called solvent dyeing (pad-thermofix application, or exhaustion dyeing processes in dyeing machines).

The new optical brighteners according to the present invention can further be added to, or incorporated in, the materials before or during their shaping. Thus they can for example be added to the compression moulding composition or injection moulding composition during the manufacture of films, sheets (for example milling into hot polyvinyl chloride) or mouldings.

Due to their stability under usual polycondensation conditions, i.e. increased temperature of up to 300° C and reduced pressure (cf. C. Eckhardt and H. Hefti J. Soc. Dyers and Colourists, 87, 365–370, 1971), whenever fully synthetic or semi-synthetic organic materials are being shaped by spinning processes or via spinning compositions, the optical brighteners can be applied to such materials by the following methods:

Addition to the starting substances (for example monomers) or intermediates (for example precondensates or prepolymers), that is to say before or during the polymerisation, polycondensation or polyaddition, Powdering onto polymer chips or granules for spinning compositions, Bath dyeing of polymer chips or granules for spinning compositions, Metered addition to spinning melts or spinning solutions, and Application to the tow before stretching.

The new optical brighteners according to the present invention can, for example, also be employed in the following use forms:

a. Mixed with dyestuffs (shading) or pigments (coloured or especially, for example, white pigments) or as an additive to dye baths or printing, discharge or resist pastes. Also, for the after-treatment of dyeings, prints or discharge prints, b. Mixed with so-called "carriers", wetting agents, plasticisers, swelling agents, anti-oxidants, light protection agents and heat stabilisers and chemical bleaching agents (chlorite bleach and bleaching bath additives), c. Mixed with crosslinking agents or finishes (for example starch or synthetic finishes), and in combination with the most diverse textile finishing processes, especially synthetic resin finishes (for example crease-proof finishes such as "wash-and-wear", "permanent-press" or "on-iron"), as well as flameproof finishes, soft handle finishes, anti-soiling finishes or antistatic finishes, or antimicrobial finishes.

d. Incorporation of the optical brighteners into polymeric carriers (polymerisation, polycondensation or polyaddition products), in a dissolved or dispersed form, for use, for example, in coating agents, impregnating agents or binders (solutions, dispersions, and emulsions) for textiles, fleeces, paper and leather.

e. As additives to so-called "master batches".

f. As additives to the most diverse industrial products in order to render these more marketable (for example improving the appearance of soaps, detergents and pigments).

g. In combination with other optically brightening substances.

h. In spinning bath preparations, that is to say as additives to spinning baths such as are used for improving the slip for the further processing of synthetic fibres, or from a special bath before the stretching of the fibre, i. As scintillators for various purposes of a photographic nature such as, for example, for electrophotographic reproduction or supersensitisation for the optical brightening of photographic layers, optionally in combination with white pigments such as, for example, $TiO_2$.

If the brightening process is combined with textile treatment methods or finishing methods, the combined treatment can in many cases advantageously be carried out with the aid of appropriate stable preparations, which contain the optically brightening compounds in such concentration that the desired brightening effect is achieved.

In certain cases, the brighteners are made fully effective by an after-treatment. This can, for example, represent a chemical treatment (for example acid treatment), a thermal treatment (for example heat) or a combined chemical/thermal treatment. Thus, for example, the appropriate procedure to follow in optically brightening a series of fibre substrates, for example polyester fibres with the brighteners according to the invention is to impregnate these fibres with the aqueous dispersions (or, where appropriate, solutions) of the brighteners at temperatures below 75° C, for example at room temperature, and to subject them to a dry heat treatment at temperatures above 100° C, it being generally advisable additionally to dry the fibre material beforehand at a moderately elevated temperature, for example at not less than 60° C and up to about 130° C. The heat treatment in the dry state is then advantageously carried out at temperatures between 120° and 225° C, for example by heating in a drying chamber, by ironing within the specified temperature range or by treatment with dry, superheated steam. The drying and dry heat treatment can also be carried out in immediate succession or be combined in a single process stage.

The amount of the new optical brighteners to be used according to the invention, relative to the material to be optically brightened, can vary within wide limits. A distinct and durable effect is already achievable with very small amounts, in certain cases, for example, amounts of 0.0001 percent by weight. However, amounts of up to about 0.8 percent by weight and at times up to about 2 percent by weight can also be employed. For most practical purposes, amounts between 0.0005 and 0.5 percent by weight are of preferred interest.

In the examples, the parts, unless otherwise stated, are always parts by weight and the percentages are always percentages by weight. Unless otherwise stated, melting points and boiling points are uncorrected.

EXAMPLE 1

6.5 g of crude naphthalene-1,4-dicarboxylic acid in 60 ml of toluene are heated with 6.1 ml of thionyl chloride and 0.1 ml of pyridine under reflux for about one-half hour. The solution is completely evaporated in vacuo and the residue (naphthalene-1,4;-dicarboxylic acid dichloride) is taken up, at room temperature, in a solution of 10.3 g of 2-amino-4-methylsulphonylphenol in 30 ml of pyridine. The solution is heated under reflux for 1 hour, 60 ml of dibutyl phthalate are added and 35 to 40 ml of solvent are distilled off over the course of one hour whilst passing in the nitrogen, in order to cyclise the acid amide of the formula (27)

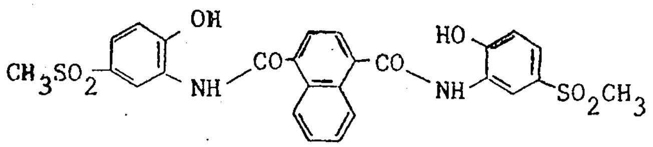

formed as an intermediate. As the temperature rises, the product which initially has separated out as an oil redissolves. After stirring for one-half hour at 320°–330° C, the mixture is left to cool and is diluted with 40 ml of alcohol. The precipitate is filtered off and washed with 10 ml of ethyl acetate and three times with 10 ml of alcohol, and after drying 10.0 g of crude dibenzoxazolyl compound of the formula (28)

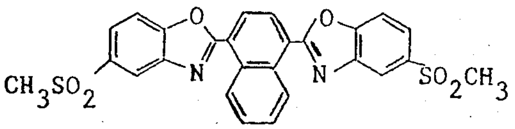

are obtained. Repeated recrystallisation from dimethylformamide with the aid of active charcoal and fuller's earth yields yellowish small needles of melting point 331°–332° C.

EXAMPLE 2

If the procedure described in Example 1 is followed but 2-amino-4-phenylsulphonyl-phenol or 2-amino-4-ethylsulphonylphenol is used as the aminophenol component, the dibenzoxazoles of the formulae (29)

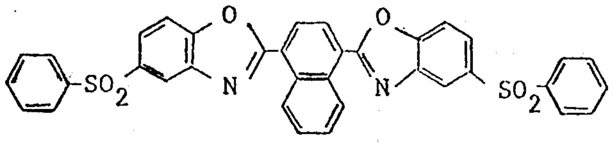

melting point 284°–285° C (recrystallised from dimethylformamide and o-dichlorobenzene) and (30)

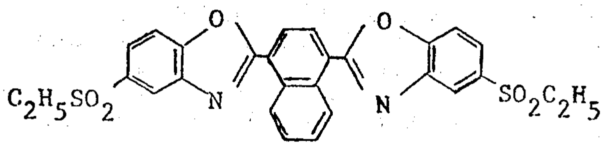

melting point 283°–284° C (recrystallised from dimethylformamide and o-dichlorobenzene) are respectively obtained.

EXAMPLE 3

6.35 g of naphthalene-1,4-dicarboxylic acid dichloride are added to a solution of 13.2 g of 2-amino-4-benzyl-sulphonylphenol in 40 ml of pyridine and the mixture is heated under reflux for 2 hours. The bulk of the solvent is evaporated off in vacuo and about 40 ml of methanol are added. After cooling to room temperature, the product which has precipitated is filtered off, washed with methanol and dried. 10.8 g of acid amide of melting point 283°–85° are obtained.

10.4 g of this acid amide are heated for 1 hour under reflux with 9.1 ml of phosphorus oxychloride and 25 ml of dichlorobenzene, whereupon benzoxazole ring closure with evolution of hydrogen chloride takes place. Finally, 6 ml of solvent are distilled off under normal pressure and the residual solvent is then distilled off in vacuo. The residue is boiled up in approx. 25 ml of methylcellosolve, the mixture is cooled and the precipitate is filtered off. After drying, a yellowish product of the formula (31)

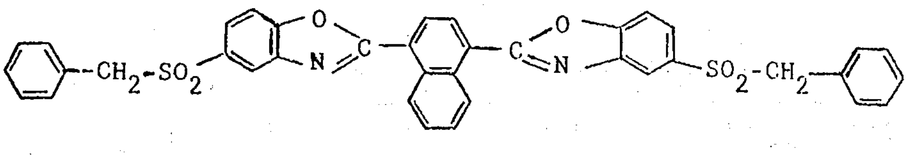

of melting point 270° to 271° is obtained. It is purified by recrystallisation from chlorobenzene, with the aid of fuller's earth.

The compounds of the general formula (32)

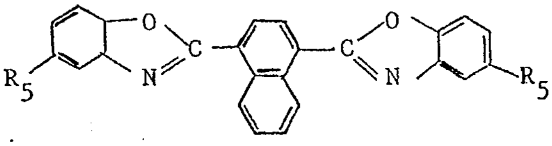

described in Table I can be manufactured similarly.

Table I

| Compound of the formula | $R_5$ | | Melting point |
| --- | --- | --- | --- |
| (33) | 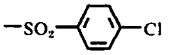 | | 306° |
| (34) | $-SO_2-(CH_2)_2-CH_3$ | | 257° |
| (35) [1] | $-SO_2-CH_2Cl$ | | 284° |
| (36) | 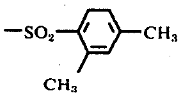 [2] | Mixture | 168° |
| | 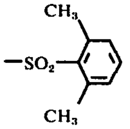 | | |
| (38) | 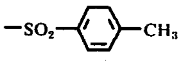 [2] | Mixture | 242° |
| | 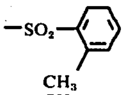 | | |
| (40) | 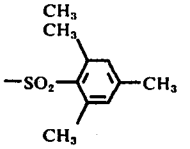 | | 246° |
| (41) | 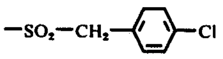 | | 350° |

[1] Instead of dichlorobenzene, chlorinated biphenyl (Aroclor 1221 Monsanto) is used in the cyclisation.
[2] Main component.

Table II

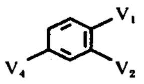

| $V_1$ | $V_2$ | $V_4$ | Melting point |
| --- | --- | --- | --- |
| Cl | $NO_2$ | 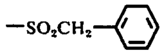 | 138° |
| OH | " | " | 174° |
| " | $NH_2$ | " | 186° |
| OH | $NO_2$ | 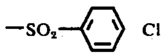 | 193° |
| " | $NH_2$ | " | 185° |
| OH | $NO_2$ | $-SO_2-CH_2CH_2CH_3$ | 100° |

Table II -continued

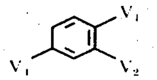

| $V_1$ | $V_2$ | $V_4$ | Melting point |
| --- | --- | --- | --- |
| OH | $NH_2$ | " | 140° |
| Cl | $NO_2$ | 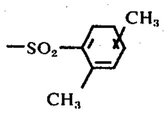 | 123° |
| OH | " | " | 105° |
| " | $NH_2$ | " | approx. 156° |
| Cl | $NO_2$ | 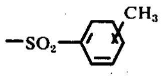 | 90° |
| OH | " | " | 110° |
| " | $NH_2$ | " | |
| Cl | $NO_2$ | 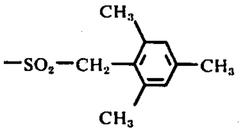 | 156° |
| OH | " | " | 171° |
| " | $NH_2$ | " | 187° |
| Cl | $NO_2$ | 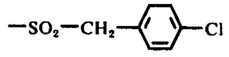 | 145° |
| OH | " | " | 197° |
| OH | $NH_2$ | " | 217° |

EXAMPLE 4

5.8 g of 4-(benzoxazolyl-(2'))-1-napthoic acid (DAS No. 1,302,052) in 2.2 ml of thionyl chloride, 40 ml of chlorobenzene and 0.8 ml of pyridine are heated to the reflux temperature for 1 hour. After complete evaporation of the solution in vacuo at 70°, a solution of 3.9 g of 2-amino-4-methylsulphonylphenol in 30 ml of pyridine is added to the acid chloride obtained, whilst stirring, and the mixture is heated under reflux for 1 hour. The solution is again completely evaporated in vacuo and the residue is stirred with 60 ml of methanol. The product which has precipitated is filtered off, washed with methanol and dried. 7.3 g of the acid amide of the formula

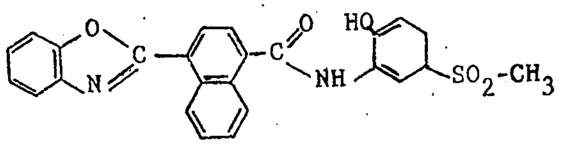

of melting point 282°–283° are obtained.

This acid amide is introduced into 50 ml of trichlorobenzene and after adding 0.23 g of an anhydrous zinc chloride the mixture is stirred for 1½ hours at the reflux temperature. After cooling, 20 ml of methanol are added and the product which has precipitated is filtered off, washed with methanol and dried. 6.7 g of the compound of the formula (43)

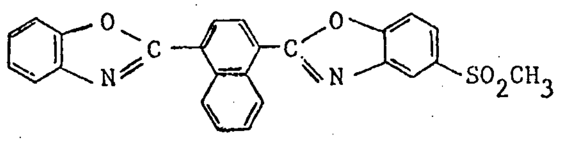

of melting point 248° are obtained. The compound is purified by recrystallisation from dimethylformamide and o-dichlorobenzene (melting point unchanged).

EXAMPLE 5

9.9 g of naphthalene-1,4-dicarboxylic acid dichloride are added to a solution of 7.8 g of 2-amino-4-methylsulphonylphenol and 8.5 g of 2-amino-4-ethylsulphonylphenol in 40 ml of pyridine, the mixture is heated under reflux for 2 hours, 60 ml of dibutyl phthalate are added and 60 ml of solvent are distilled off over the course of 1 hour whilst passing in nitrogen. After cooling, the product which has precipitated is filtered off, repeatedly washed with ethyl acetate and then with alcohol, dried and recrystallised from dimethylformamide. 8.7 g of a mixture of the compounds of the formulae (44)

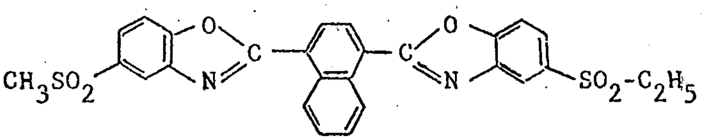

(28) and (30) are obtained, which after further recrystallisation from dimethylformamide and o-dichlorobenzene with the aid of fuller's earth melts at 300°–302°.

EXAMPLE 6

The compounds described in Table III (as mixtures, where relevant), of the general formula (45)

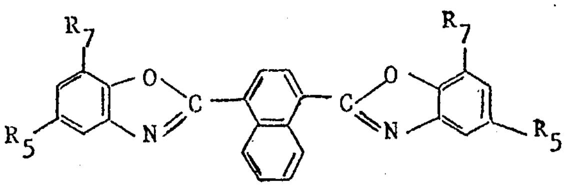

can be manufactured in a similar manner to the products mentioned in Examples 1 and 3.

Table III

| Compound of the formula | $R_5$ | $R_7$ |
|---|---|---|
| (46) | 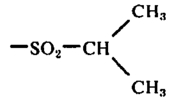 | H |
| (47) | $-SO_2-(CH_2)_3-CH_3$ | H |
| (48) | 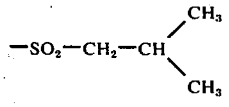 | H |
| (49) | 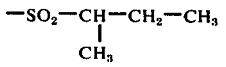 | H |
| (50) | $-SO_2-(CH_2)_4-CH_3$ | H |
| (51) | 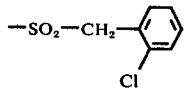 | H |
| (52) | 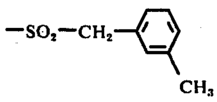 | H |
| (53) | 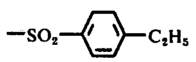 | H |
| (54) | 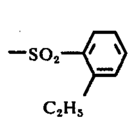 | H |

Table III-continued

| Compound of the formula | $R_5$ | $R_7$ |
|---|---|---|
| (55) | 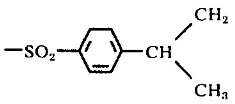 | H |
| | 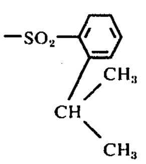 | H |
| (56) | 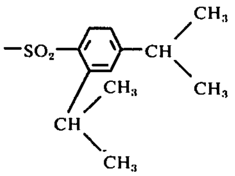 | H |
| (57) | 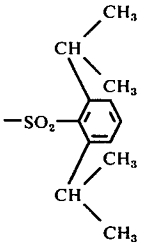 | H |
| (58) | $-SO_2CH_3$ | $-Cl$ |
| (59) | $-SO_2CH_3$ | $-CH_3$ |
| (60) | $-Cl$ | $-SO_2CH_3$ |
| (61) | $-Cl$ | $-SO_2-$ 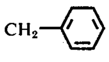 |
| (62) | $-Cl$ | 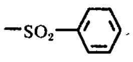 |

EXAMPLE 7

If the procedure described in Example 1 is followed but 2-amino-5-methyl-sulphonyl-phenol is used as the aminophenol component, the compound of the formula

(63) 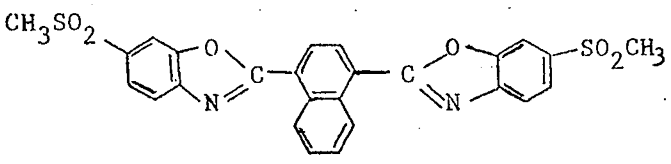

melting point 359°–361° (recrystallised from dimethylformamide and trichlorobenzene) is obtained.

2-Amino-5-methylsulphonyl-phenol, an intermediate product for the compound of the formula (63) can be manufactured as follows:

The moist sulphochloride of the formula

(64) 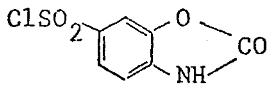

obtained by sulphochlorination of 350 g of 1,3-benzoxazolone is introduced in portions, at 5°–10° C (with cooling) into a well-stirred solution of 164.2 g of sodium sulphite in 1.5 l of water, whilst simultaneously adding dropwise 10% strength aqueous sodium hydroxide solution (approx. 1,150 ml), as a result of which the pH is kept constantly at 8. When the main reaction has subsided, the mixture is additionally warmed for 30 minutes at 55° (with further addition of sodium hydroxide solution), the solution is cooled and acidified with 200 ml of concentrated hydrochloric acid and the product which has precipitated is filtered off and washed with ice water. After drying in a high vacuum at 50°, 134.4 g of the crude sulphinic acid of the formula

(65) 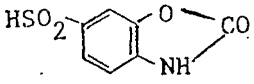

of melting point 156°–158° (after recrystallisation from water) is obtained.

95.5 ml of dimethylsulphate are added to a suspension of 99.6 g of crude sulphinic acid of the formula (65) in 250 ml of acetone and 150 ml of water and the mixture is stirred for 40 minutes at 40° C. The acid liberated by the reaction is then neutralised continuously at 40° by dropwise addition of 30% strength sodium hydroxide solution (approx. 120 ml) so that the pH constantly varies between 3.5 and 4. Hereupon the starting product completely dissolves, after which the reaction product crystallises out. After completion of the reaction the mixture is adjusted to pH 6 and the acetone is stripped off in vacuo. The precipitate is filtered off, washed with water and dried. 68.0 g of crude methylsulphone of the formula

(66) 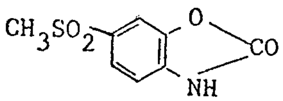

of melting point 267°–269° C (twice recrystallised from methanol-water) are obtained.

42.7 g of crude methylsulphone of the formula (66) in 60 ml of 30% strength sodium hydroxide solution and 50 ml of water are heated for 2 hours under reflux. The cooled solution is neutralised with concentrated hydrochloric acid to pH 6–7 (evolution of $CO_2$) and the precipitate is filtered off at 0° and washed with ice water. After drying, 27.8 g of aminophenol of the formula

(67) 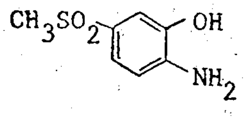

of melting point 195°–197° C are obtained (in the form of small needles after recrystallisation from water).

The compound of the formula

(68) 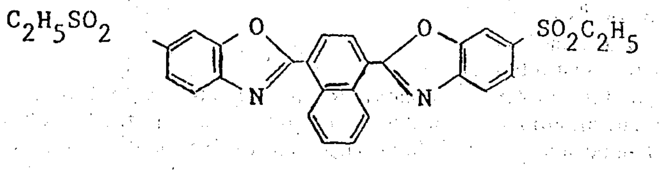

can be manufactured in a similar manner.

EXAMPLE 8

100 parts of polyester granules of polyethylene glycol terephthalate are intimately mixed with 0.05 part of the compound of the formula (28) and the mixture is fused at 285° C whilst stirring. After spinning the spinning composition through customary spinnerets, strongly brightened polyester fibres of good fastness to light are obtained. If instead of the compound of formula (28) a compound of the formula (29), (30), (31), (33), (34), (35), (36), (38), (40), (41), (43) or (44) is used, similar results are obtained.

EXAMPLE 9

The polyester fabric (for example "Dacron") is padded at room temperature with an aqueous dispersion which contains 2 g of the compound of the formula (31) and 1 g of an addition product of about 8 mols of ethylene oxide to 1 mol of p-tert. octylphenol per liter, and is dried at about 100° C. The dry material is subsequently briefly subjected to a heat treatment at 220° C. The material treated in this way shows a strong brightening effect with good fastness to light.

If instead of the compound of the formula (31) a compound of the formula (36), (38), (40), (43) or (44) is employed, similar results are obtained.

EXAMPLE 10

An intimate mixture of 100 parts of polyvinyl chloride, 3 parts of stabiliser (Advastat BD 100: Ba/Cd Complex), 2 parts of titanium dioxide, 59 parts of dioctyl phthalate and 0.01 to 0.2 part of one of the compounds of the formulae (28), (30), (31), (34), (41), (43) or (44) is milled on a calender at 150° to 155° C to give a sheet. The opaque polyvinyl chloride sheet thus obtained has a substantially higher degree of whiteness than a sheet which does not contain the optical brightener.

EXAMPLE 11

100 parts of polystyrene and 0.1 part of the compound of the formula (43) are fused for 20 minutes at 210° in a tube of 1 cm diameter, with exclusion of air. After cooling, an optically brightened polystyrene composition of good fastness to light is obtained.

EXAMPLE 12

A casting composition of 10 g of polyacrylonitrile, 0.2 g of titanium dioxide (anatase modification) as the delustering agent and 40 ml of dimethylformamide, which contains 5 mg of the compound of the formula (43), is cast on a glass plate and spread by means of a metal rod to give a thin film. After drying, the film is greatly brightened.

EXAMPLE 13

A 13% strength casting composition of acetyl cellulose in acetone which contains — relative to the plastics solids content — 2% of anatase (titanium dioxide) as the delustering agent, and 0.04% of the compound of the formula (28), is cast on a glass plate and spread by means of a metal rod to give a thin film. After drying, the film shows a substantially higher degree of whiteness than a film manufactured in the same way, which does not contain an optical brightener.

I claim:

1. A 1,4-bix-benzoxazolyl-(2')-naphthalene, corresponding to the formula

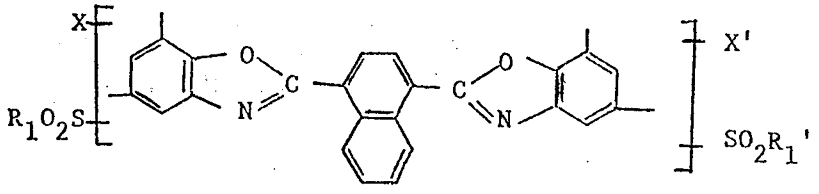

wherein $R_1$ and $R_1'$ independently of one another denote alkyl with 1 to 6 carbon atoms which is optionally substituted by chlorine, phenyl which is optionally substituted by chlorine or alkyl with 1 to 4 carbon atoms, or phenylalkyl with 1 to 3 carbon atoms in the alkyl part which is optionally substituted by chlorine or methyl in the phenyl part and X and X' independently of one another denote hydrogen, chlorine or alkyl with 1 to 4 carbon atoms.

2. A symmetrical 1,4-bis-benzoxazolyl-(2')-naphthalene according to claim 1, corresponding to the formula

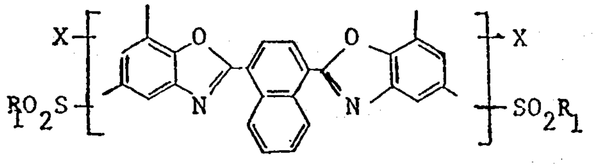

wherein $R_1$ denotes alkyl with 1 to 6 carbon atoms which is optionally substituted by chlorine, phenyl which is optionally substituted by chlorine or alkyl with 1 to 4 carbon atoms or phenylalkyl with 1 to 3 carbon atoms in the alkyl part which is optionally substituted by chlorine or methyl in the phenyl part, and X denotes hydrogen, chlorine or alkyl with 1 to 4 carbon atoms.

3. A 1,4-bis-benzoxazolyl-(2')-naphthalene according to claim 1, corresponding to the formula

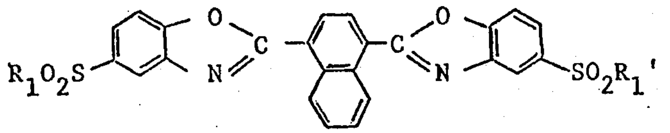

wherein $R_1$ and $R_1'$ independently of one another denote alkyl with 1 to 6 carbon atoms which is optionally substituted by chlorine, phenyl which is optionally substituted by chlorine or alkyl with 1 to 4 carbon atoms, or phenylalkyl with 1 to 3 carbon atoms in the alkyl part which is optionally substituted by chlorine or methyl in the phenyl part.

4. A symmetrical 1,4-Bis-benzoxazolyl-(2')-naphthalene according to Claim 1, corresponding to the formula

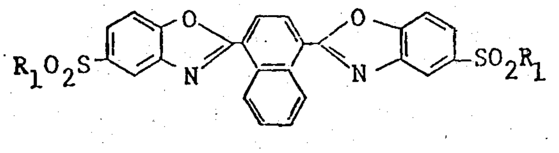

wherein $R_1$ denotes alkyl with 1 to 6 carbon atoms which is optionally substituted by chlorine, phenyl which is optionally substituted by chlorine or alkyl with 1 to 4 carbon atoms, or phenylalkyl with 1 to 3 carbon atoms in the alkyl part which is optionally substituted by chlorine or methyl in the phenyl part.

5. A 1,4-bis-benzoxazolyl-(2')-naphthalene according to claim 1, corresponding to the formula

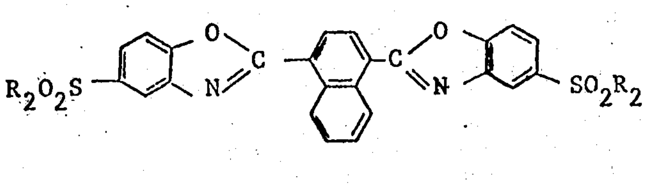

wherein $R_2$ denotes methyl, ethyl, phenyl or benzyl.

* * * * *